United States Patent
Schalkhammer et al.

(10) Patent No.: US 6,669,906 B1
(45) Date of Patent: Dec. 30, 2003

(54) REINFORCED CLUSTER OPTICAL SENSORS

(76) Inventors: Thomas Schalkhammer, A-3072, Kasten 105 (AT); Fritz Pittner, Khekgasse 40-42/11, A-1230 Vienna (AT); Georg Bauer, Güttlfeld 72, A-4070 Eferding (AT)

( * ) Notice: Subject to any disclaimer, the term of this patent is extended or adjusted under 35 U.S.C. 154(b) by 0 days.

(21) Appl. No.: 09/403,488
(22) PCT Filed: Apr. 20, 1998
(86) PCT No.: PCT/AT98/00101
§ 371 (c)(1), (2), (4) Date: Oct. 22, 1999
(87) PCT Pub. No.: WO98/48275
PCT Pub. Date: Oct. 29, 1998

(30) Foreign Application Priority Data

| Apr. 22, 1997 | (AT) | 680/97 |
| Sep. 30, 1997 | (AT) | 1655/97 |
| Sep. 30, 1997 | (AT) | 1656/97 |

(51) Int. Cl.[7] ............ G01N 1/00; G01N 15/00; G01N 33/53; C12Q 1/68
(52) U.S. Cl. ............ 422/50; 422/68.1; 435/6; 435/7.1
(58) Field of Search ............ 422/50, 68.1; 435/6, 435/7.1; 436/501

(56) References Cited

U.S. PATENT DOCUMENTS

| 4,299,916 A | * | 11/1981 | Litman et al. ............ 435/6 |
| 5,017,009 A | * | 5/1991 | Schutt et al. ............ 358/338 |
| 5,507,936 A | | 4/1996 | Hatschek et al. ............ 204/412 |
| 5,611,998 A | | 3/1997 | Aussenegg et al. ......... 422/82.05 |
| 5,632,957 A | * | 5/1997 | Heller et al. ............ 422/68.1 |

FOREIGN PATENT DOCUMENTS

| EP | 0300990 | 1/1989 |
| EP | 0677738 | 10/1995 |
| EP | 0702228 | 10/1997 |
| WO | 9005295 | 5/1990 |
| WO | 9515496 | 6/1995 |

OTHER PUBLICATIONS

Sternberger et al., J. of Histochemistry and Cytochemistry, vol. 18, No. 5, pp. 315–333, 1970.*

* cited by examiner

*Primary Examiner*—Ardin H. Marschel
(74) *Attorney, Agent, or Firm*—Dykema Gossett PLLC

(57) ABSTRACT

A new optical sensor is presented, characterized in, that at distance of less than 1 μm to an electromagnetic waves reflecting layer, analyte-interacting linkers are immobilized onto which elektrically-conducting clusters with a diameter smaller than 500 nm are bound.

15 Claims, 3 Drawing Sheets

REINFORCED CLUSTER OPTICAL SENSORS

This is a 371 application of PCT/AT98/00101 Apr. 20, 1998.

BACKGROUND AND SUMMARY OF THE INVENTION

The invention relates to a new principle of measurement for constructing sensors and for use in bioinformatics. The technology is based on a new plasmon optical measurement setup applying clusters, by means of which nucleic acids, proteins or their ligands can be detected. The analytes cited above induce the binding or dissociation of metallic clusters, which have been or will be bound at a defined distance to a reflecting, preferentially electron-conducting surface. The binding or dissociation is transduced into a clearly detectable optical signal through resonant enhancement of clusters interacting with their mirror dipols. Nowadays there is a strong demand for fast, simple and cheap test procedures in medical diagnostics, food and environmental analysis. Sensitivity, selectivity and reliability are absolutely required. At the same time, ever increasing requirements for sensitivity, selectivity and reliability combined with maximal simplicity of the measurement process are demanded. The present invention aims on reducing technical restrictions of established measurement procedures through a novel one step test setup. Rapid and secure test-kits for clinical and lab use can be set up based on this technology. As possible fields of application, the diagnosis of urinary tract infections, screening of allergens, quantification of bacterial contamination of food, blood-glucose can be cited.

The parts of the invention provided with reference signs are to be assigned as follows: 1=support material, 2=reflecting layer (preferentially electron-conducting metal or cluster layer), 3=0–500 nm distance layer, 4=nanometric, non-conducting particles, 5=chemically reactive surface attachment, 6=linker (e.g. DNA, proteins, . . . ), 7=cluster, 8=analyte, 9=split linker (e.g. split by the analyte), 10=non-split linker, 11=after coupling of the catalytically reactive analyte, 12=sensor setup after splitting of the linker, 13=dissociation of the cluster with an attached part of the linker, 14=free split cluster-linker-conjugates, 15=electrodes at or near the chip or magnet, 16=analyte-binding molecule, e.g., DNA, protein, . . . , 17=analog to the analyte.

The sensor is formed of a metal layer, on a substrate material, an inert distance layer e.g., deposited by spin coating or chemical vapor deposition, on top of which individual linker molecules with bound clusters are coupled. The diameter of the clusters is preferentially chosen to be smaller than 40 nm. If the analyte interacts with the linker, it induces either changes in the extent of surface coverage of the cluster layer on a molecular scale or changes in the spatial arrangement of the bound clusters, both leading to characteristic changes of the optical appearance of the sensor surface. The surface colored by the abnormal optical effect is changed because of the catalytic or biorecognitive activity of an analyte or the addition of an enzymatically active component. Metal clusters layers with a cluster diameter smaller than 500 nm preferentially smaller than 40 nm (to suppress multipol peaks in the spectrum) possess strong and narrow reflection minima. Their spectral position is extremely dependent on their spatial arrangement, especially the distance of the cluster layer to the electron conducting surface.

The sensor setup can transduce even minute changes in the extent of surface coverage with clusters into a clearly visible optical signal, either a strong change in absorption at a defined wavelength or a spectral shift of the absorption maximum. According to the invention it is possible to convert biorecognitive binding processes and catalytic activity of proteins by the application of surface enhanced clusters into an optical signal (=color change of sensor surface).

The sensitivity of the chip can roughly be estimated as follows: Clusters of a diameter of 25 nanometers are arranged in a two dimensional lattice of 100 nanometers and where each cluster is bound via one analyte to the surface. At an optical resolution of $\frac{1}{10}$ mm (observation of a field of 100×100 micrometers gives a meaningfull signal) a change of 10% of the maximum signal equals $2\times10e5$ molecules. This sensitivity has been proved with an antigen—antibody setup. The application of catalytically active analytes increases the sensitivity several orders of magnitude and allows single molecule detection.

Nanoclusters (preferenually silver, aluminum or gold cluster) can be bound by means of so-called biochemical linkers at a defined distance to the metallized surface. A detectable signal will result if these linker are either formed or cut by biochemical recognition or by catalysis, or if their spatial arrangement is altered. According to the invention, i.e., oligonucleotides are applied as linkers which can then be cut by the analyte (e.g. restriction enzymes from microorganisms) (see FIGS. 1 and 2). Many pathogenic microorganisms express specific restriction endonucleases and can therefore be detected by means of the new sensor without expensive instrumentation at the local physician or in the laboratory. This enables, e.g., the differential diagnosis of urinary tract infections through direct detection of *E. coli* (responsible for 60% of all urinary tract infections). A fast and reliable screening method for bacterial contamination of foods can also be constructed.

The technology is based on enhanced cluster plasmons, which transduce in a very simple and reproducible manner the activity of a chemically reactive species into an optical signal.

The sensor setup essentially is built in a way that:
1. at a distance of less than 1 $\mu$m to
2. a reflecting surface, preferentially an electron conducting layer
3. linkers are immobilized, onto which
4. directly or indirectly electrically conducting clusters are bound.

Metal clusters can therefore be coupled to the surface of an inert (non-reactive) polymer and can be arranged on the polymer surface via biochemical linkers in a defined distance to the metal surface. The linkers can either be cut or their spatial arrangement can be altered through biochemical recognition or catalysis both leading to an optically detectable signal. In a DNA/RNA-test-system oligonucleotides can be used as linkers, which will consecutively be cut by restriction enzymes from microorganisms.

This invention differs substantially from the subject of the invention of the Austrian Patent No. 403,746 and U.S. Pat. No. 5,611,998 in substantial structural features: The invention does not involve a reactive matrix preferentially meant to perform volume changes. The setup described in this application is based on alterations of surface coverage with clusters bound via analyte-interactive linkers at a defined distance to an electron conducting layer.

The term "abnormal properties of a metal film" means a strong absorption maximum in the visible spectrum, resulting from localization of the conductivity electron plasma within the spatial boarders of nanometric particles. This spatial localization contrasts to the free mobility of electrons in a macroscopic piece of metal (the free mobility of electrons there is responsible for a strong unspecific reflection, generally called metallic luster).

A metal cluster at a defined distance from a metal surface interacts with the electron gas of the neighboring metal layer. At a certain distance of the absorbing cluster layer to the metal surface the electric field reflected from the metal surface has the same phase like the incoming fields. The resulting feedback mechanism enhances the effective coefficient of absorption of the cluster layer. Since at a given thickness of the distance layer the optimum phase enhancement depends only on the frequency of the radiated light, the system can be spectrally characterized by a very narrow reflection minimum. The intensity of the absorption band is directly proportional to the number of interacting clusters over a wide range of surface coverage. Any reduction of the number of clusters by chemically induced cut-off results in a lowering of the absorption of the resonant system. At a high surface coverage a spectral shift due to a change in cluster-cluster interactions can be observed (e.g. see FIG. 2).

The optical characteristics of the sensor can be described by either the stratified medium theory or the CPS-theory (developed by Chance, Prock and Silbey). These theories focus either on optical thin films or on the behaviour of a polarizable particle in vicinity to a metal surface. The stratified medium theory can be applied for the calculation of any kind of optical thin-films. It is based on the solution of Maxwell's equations under the condition that the interfaces and the thicknesses of the different layers are given.

In order to apply the stratified medium theory the optical constants of all four layers (substrate surface, distance layer, linker layer and island layer) have to be known. The optical constants of the island film strongly depend on chemical and physical parameters and therefore have to be determined experimentally. In order to determine the optical constants at least two independent measurements of reflection and transmission spectra of the island film have to be known. From calculations of optimal conditions it can be concluded that at a mean mass-thickness of 5 nm a maximum of the signal will be obtained. Dependent on the number of linker-bound clusters the reflection signal can vary up to three orders of magnitude. At optimized enhancement conditions even single clusters are visible as color change upon radiation with white light.

Due to their particle structure cluster or colloid films do not pose a barrier of diffusion to gases or fluids.

The analyte concentration can be measured with high sensitivity via visual inspection of the sensor surface. In order to reduce unspecific background absorption of the sample measurement can be carried out at two angles of observation. Whereas absorption of chromophores is independent of the angle of observation, the spectral reflection signal strongly shifts dependent on the angle. Thus by simple subtraction of both signals the background resulting from matrix effects can easily be eliminated.

According to the invention, the sensor for measurement of specific DNA and RNA sequences can be built in that only after hybridization of analyte DNA/RNA and linker nucleotide represents a restriction enzyme, cutting site. After incubation with a restriction enzyme the cut DNA/RNA with the bound cluster can then be removed by a simple washing step. Because of the temperature stability of the setup, a direct combination with PCR is feasible.

Analogously, restriction endonucleases which cut double stranded linkers can be be measured or an HIV-specffic-peptide by HIV-protease, which cuts an HIV specific peptide-linker. In order to detect bacterial restriction enzymes, the bacterial cell walls have to be broken or made permeable. The efficiency of the cell wall breakdown is decisive for the sensitivity of the test. A simple sensor can be applied in order to test activity and purity of restriction enzymes applied in molecular biological research.

DETAILED DESCRIPTION OF THE PREFERRED EMBODIMENTS

Figure 1:
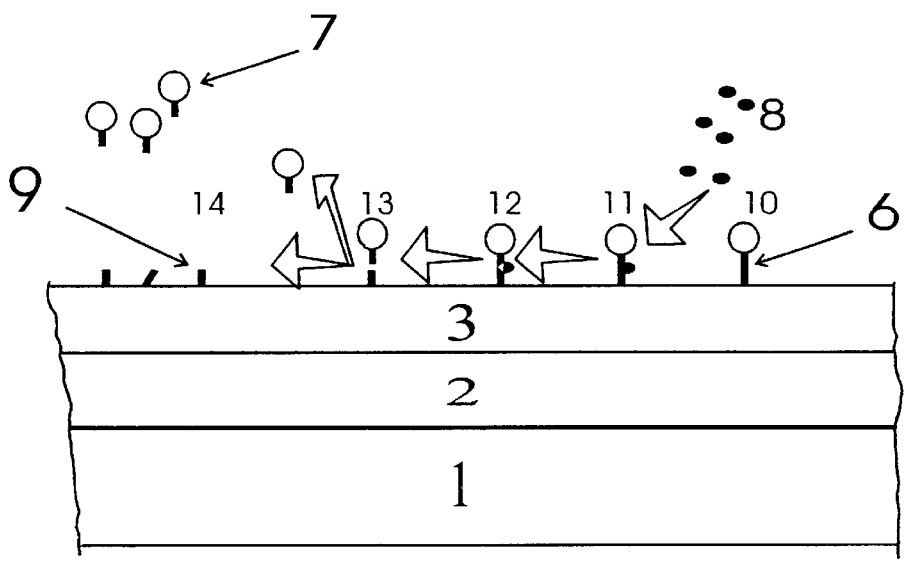
FIG. 1 shows a first embodiment of the inventive optical sensor wherein linkers are cut by biochemical recognition.
Figure 2:
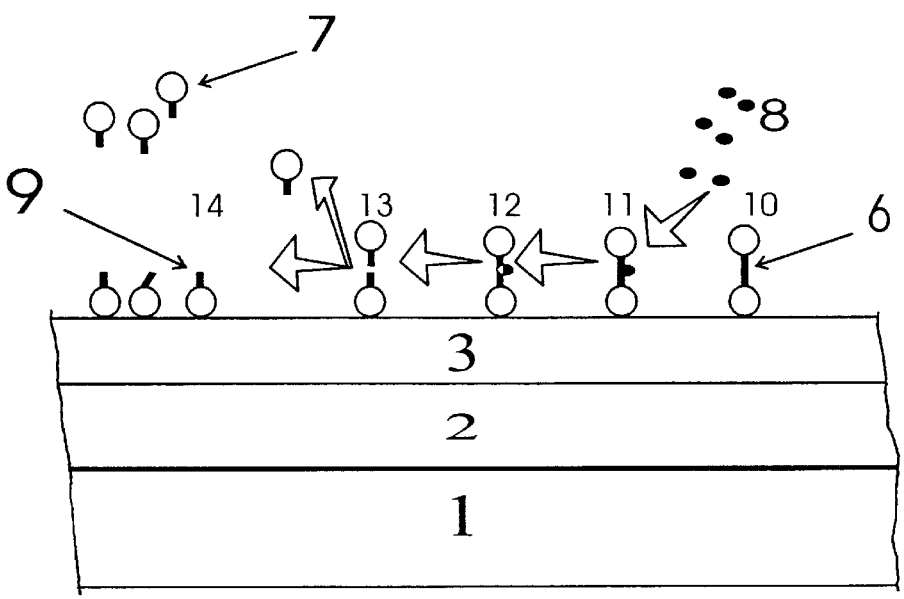
FIG. 2 shows a second embodiment wherein the spatial arrangement of the linkers is altered.

FIGS. 1 and 2 show the technical realization of two different setups of the inventive optical sensor, which include a support material 1, a reflecting layer 2 and a 0 to 500 nm distance layer 3 having attached linkers 6 (e.g., DNA, proteins, . . . ) with clusters 7. Reference numeral 9 represents a split linker (e.g. split by the analyte 8). Reference numerals 10 to 14 show the linker 6 in different states, 10 being a non-split linker, 11 after coupling of the catalytically reactive analyte 8, 12 being the sensor setup after splitting of the linker, 13 showing dissociation of the cluster with an attached part of the linker, 14 being free split clusterlinker conjugates. A detectable signal will result if these linkers are either formed or cut by biochemical recognition or by catalysis (FIG. 1), or if their spatial arrangement is altered (FIG. 2).

The following four examples are typical setups for the technical realization of the sensor.

Figure 3:
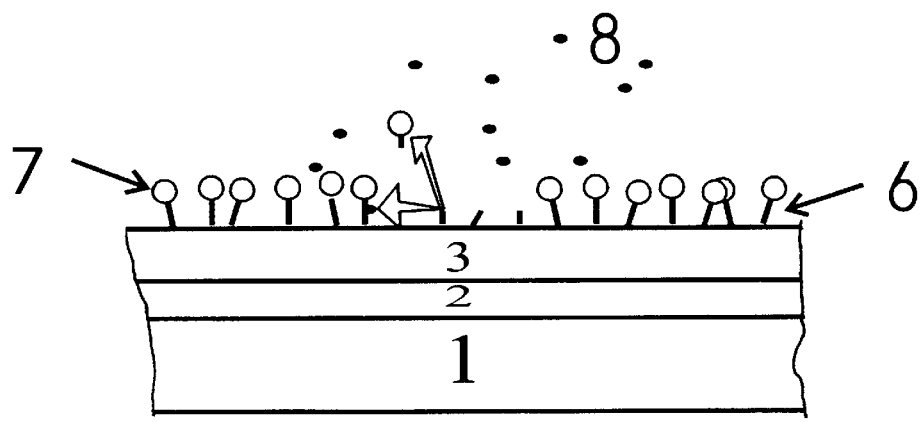
FIG. 3 shows a third embodiment which includes a nanometric thin film as an inert interlayer and a reflecting layer made of Al.

Setup 1. (see FIG. 3)

A statistic coupling of linkers according to standard chemical protocols onto a nanometric thinfilm produced via Polymer-spinning.

Figure 4:
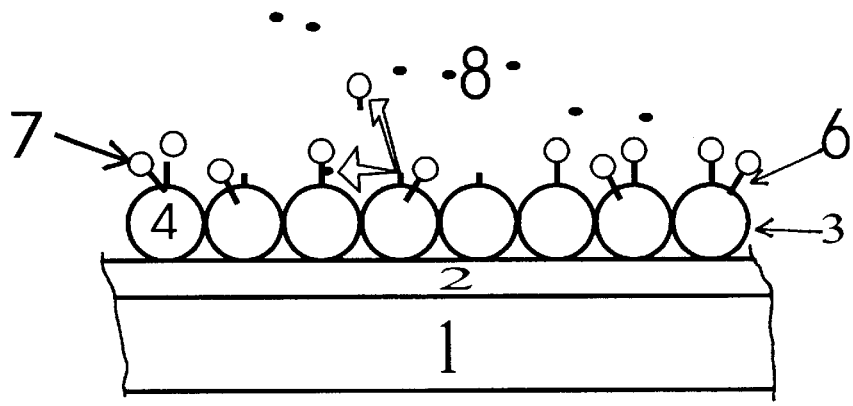
FIG. 4 shows a variant of the inventive sensor having nanometric particles as an inert interlayer.

Setup 2. (see FIG. 4)

Use of nanometric particles, i.e., made from polystyrene, as distance layer is a way to achieve a constant distance between clusters and metal surface, even if the metal surface is not smooth at a nanometric scale or curved on a macroscopic level.

Setup 3. (see FIG. 5)

This technology uses an advanced way of microstmucturing.

Figure 6:
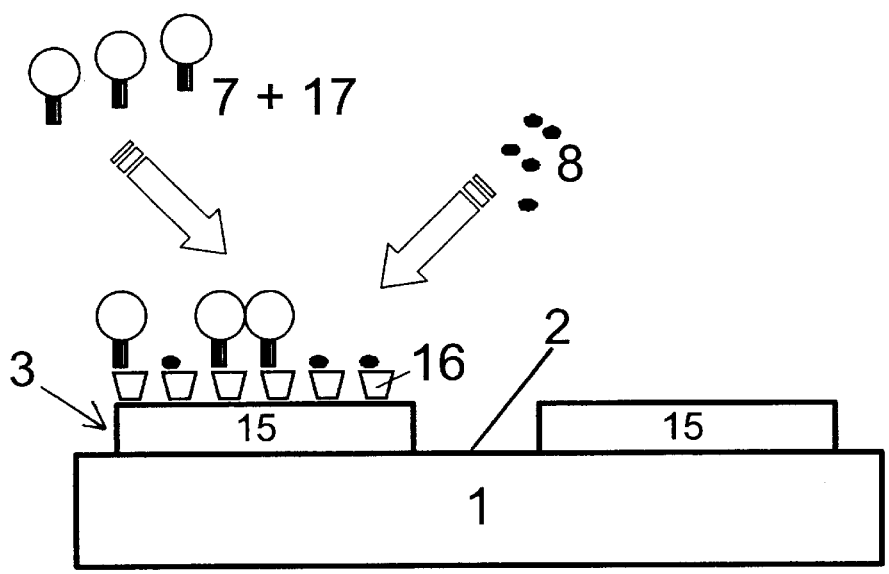
FIG. 6 shows a further variant of the inventive sensor having additional electrodes attached to the reflecting metal layer.
Figure 7:
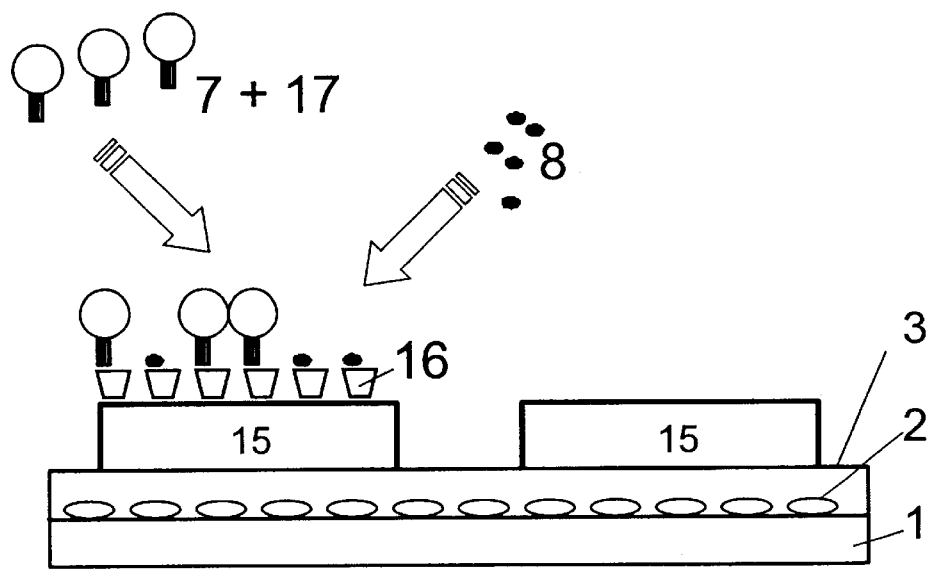
FIG. 7 shows a variant of the FIG. 6 sensor wherein the reflecting layer is made of colloid particles.

Setup 4. (see FIGS. 6 and 7)

This technology applies electrophoretic movement of clusters.

The technical realization is explained in the following examples:

Example 1 (FIG. 3): Onto PET 1 metallized with Al 2 (resistance is 2Ω/square) a 6% solution of polyhexyl-metacrylate is applied by thinfilm coating (4000 rpm, 60 sec). The surface of the thinfilm 3 is hydroxylated, carboxylated and carbonylated with oxygen-plasma. Glycosylated proteins are bound via unspecific adsorption or coupling with water soluble carbodiimide. Tetrametric Concanavaline A (ConA) 6 is added and binds to the hexose exposing surface. Thereby a hexose binding surface is created. Gold colloids 7 with 14 nm in diameter are coated with glycosylated protein (e.g. peroxidase). The aggregation of clusters or unspecific binding is prevented by addition of 0.1% Tween 20. After addition of the analyte 8 the binding process occurs under competitive reaction at the chip surface. Thus the clusters approach the metal surface to a defined distance, and the desired optical properties of a surface enhanced cluster layer are coming into effect.

Example 2: Nanometric particles from polystyrene are appropriate as a distance layer 3. A silver surface produced by evaporation is incubated with a solution of 2% cystamine in ethanol for 30 minutes, whereby a self assembly monolayer with free amino groups is formed. Nanometric particles 4, e.g., carboxylated beads, with a diameter of 50 nm, can be coupled to these amino groups via a two step EDC coupling protocol. Such beads can be coupled with the same EDC coupling protocol onto aminosilane coated steal. After the coupling reaction is completed,the nanometric spherical particles with a narrow size distribution form a dense, chemically reactive, two dimensional pattern. Onto the beads oligonucleotides O 6 with an artificially introduced amino terminus can be coupled to the carboxylated microspheres according to an EDC coupling protocol. The reactivity of EDC has to be reduced by the addition of imidazole, in order to have only highly reactive terminal oligo amino groups reacting with the carboxylated-beads.

Figure 5:
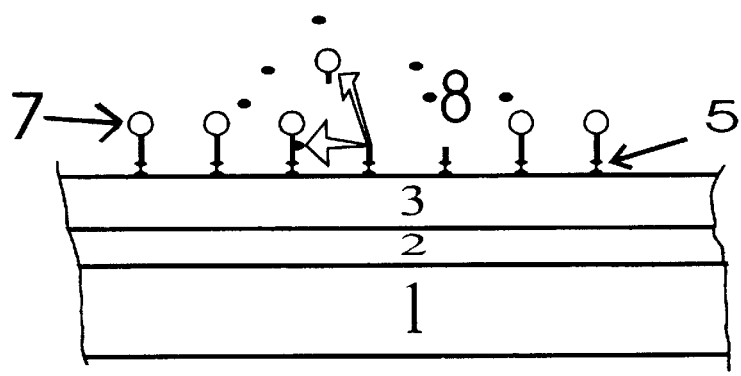
FIG. 5 shows a variant of the inventive sensor having reactive thiol groups as ordered immobilization sites.

Example 3: Carboxylated polystyrene beads are coupled to a polyhexyl metacrylate layer via a bifunctional and dissociable linker. The remaining reactive groups of the polymer are inactivated with alcohol to form ester bonds. The beads form a two dimensional ordered lattice and upon dissociation of the linker, i.e., free thiol groups 5 result at defined nanometric distances to each other (FIG. 5). The reactive thiol groups can then serve as ordered immobilization sites 5, i.e., via iodacetyl-activation.

Example 4: The sensor is set up similar to the one described in example 1. Additionally two electrodes 15, usually made from Pt, Au, Ag, Pd, or steel, are attached to the reflocting support material 1 (FIG. 6) or to the reflecting layer 3 (FIG. 7) to allow microelectrophoresis. It proved to be especially advantagous if the distance layer 3 is ion- and electrically conducting and used as one electrode. Therewith, e.g., ITO can be deposited by chemical vapour deposition or coating with an ion-conducting polymer. Applying of an electrophoretic potential induces a movement of electrically conducting clusters 7. Therewith either local concentration can be increased or unbound clusters can be removed. The duration of analysis can be remarkably reduced. In a similar setup nanomagnetic particles, e.g., metal—metal oxide, usually iron or chromium can be moved by (electro)-magnetic force.

What is claimed is:

1. An optical sensor comprising an electrically conducting, electromagnetic waves reflecting layer, said reflecting layer being made of metal or electrically-conducting colloid particles, an inert interlayer, and analyte-interacting linkers immobilized on a surface of said inert interlayer at a distance of less than 500 nm from said reflecting layer, said analyte-interacting linkers including a number of electrically-conducting colloid particles having a diameter of less than 500 nm bound thereto, interaction of an analyte with said optical sensor causing changes in the number of electrically-conducting colloid particles bound to said analyte-interacting linkers and thus leading to characteristic color changes of said optical sensor, said inert interlayer providing a constant distance between the electromagnetic wave-reflecting layer and the linker-bound colloid particles.

2. An optical sensor as claimed in claim 1, wherein said linkers are selected from the group consisting of DNA, RNA, proteins, peptides and ligands thereof.

3. An optical sensor as claimed in claim 1, wherein said linkers are cleavable by said analyte.

4. An optical sensor as claimed in claim 1, wherein the linkers comprise ds-DNA, ds-RNA or ds-synthetic analogues which can be cleaved by a restriction enzyme.

5. An optical sensor as claimed in claim 1, wherein the linkers comprise ss-DNA, ss-RNA or ds-synthetic analogues able to hydridize with the analyte.

6. An optical sensor as claimed in claim 5, wherein the double strands formed can be cleaved by a restriction enzyme not able to cleave the ss-linker.

7. An optical sensor as claimed in claim 1, wherein said electrically-conducting colloid particles bound by said linkers are synthesized by chemical means.

8. An optical sensor as claimed in claim 1, wherein the colloid particles are selected from the group consisting of silver, gold, aluminum, copper, indium and any other metal or alloy with no interfering interband transitions in the visible or near infrared region.

9. An optical sensor as claimed in claim 1, wherein the distance between the reflecting layer and the linkers is set up by attaching nanometric particles of the desired size.

10. An optical sensor as claimed in claim 1, wherein an array of linkers is formed by attaching nanometric particles to the reflecting layer.

11. An optical sensor as claimed in claim 10, wherein the array of linkers is produced by chemical imprints generated by attaching nanometric particles.

12. An optical sensor as claimed in claim 1, wherein the linkers comprise peptides or proteins which can be cleaved by a proteolytic enzymes.

13. An optical sensor as claimed in claim 1, wherein the linkers comprise antibody-antigen or receptor-ligand conjugates in which one of the partners can be replaced by the analyte.

14. An optical sensor as claimed in claim 1, wherein an optical signal is enhanced by a second population of colloid particles.

15. An optical sensor as claimed in claim 1, including electrodes or magnets tomove the colloid particle toward or away from the optical sensor.

* * * * *